(12) United States Patent
Kennedy et al.

(10) Patent No.: US 7,666,597 B2
(45) Date of Patent: Feb. 23, 2010

(54) MARKER FOR TARDIVE DYSKINESIA

(75) Inventors: James Lowery Kennedy, Toronto (CA); Clement C. Zai, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 46 days.

(21) Appl. No.: 11/538,073

(22) Filed: Oct. 3, 2006

(65) Prior Publication Data

US 2008/0081019 A1    Apr. 3, 2008

(51) Int. Cl.
*C12Q 1/68* (2006.01)
(52) U.S. Cl. ......................................................... 435/6
(58) Field of Classification Search ........................ None
See application file for complete search history.

(56) References Cited

OTHER PUBLICATIONS

Segman et al. (Molecular Psychiatry 1999 vol. 4 p. 247).*
Srivastava et al. (Pharmacogenetics and Genomics 2006 vol. 16 p. 111).*
Nikoloff et al. (The pharmacogenomics Journal 2002 vol. 2 p. 400).*
Sachdev et al. (Australian and New Zealand Journal of Psychiatry 2000 vol. 34 p. 355).*
Jonsson et al. (Psychiatric Geneicts 2003 vol. 13 p. 1).*
Accili D, et al. (1996). A targeted mutation of the D3 dopamine receptor gene is associated with hyperactivity in mice. Proc Natl Acad Sci U S A 93(5),1945-9.
Apa (1994). Diagnostic and Statistical Manual of Mental Disorders (4th edn). Washington, DC: American Psychiatric Association.
Basile VS, et al. (1999). Association of the MseI polymorphism of the dopamine D3 receptor gene with tardive dyskinesia in schizophrenia. Neuropsychopharmacology 21,17-27.
Buckland PR, et al. (1992). Changes in dopamine DI, D2 and D3 receptor mRNA levels in rat brain following antipsychotic treatment. Psychopharmacology (Berl) 106(4), 479-83.
Tardive dyskinesia and neuroleptics: from dogma to reason. Casey DE, Gardos G (ed). American Psychiatric Press, Inc., Washington DC, USA, 1986. p. 40.
D'Souza U, et al. (1997). Antipsychotic regulation of dopamine D1, D2 and D3 receptor mRNA. Neuropharmacology 36(11-12), 1689-96.
Guy W (1976). ECDEU Assessment Manual for Psychopharmacology (Revised edn). Washington, DC: Department of Health, Education and Welfare.
Gyertyan & Saghy (2004). Effects of dopamine D3 receptor antagonists on spontaneous and agonist-reduced motor activity in NMRI mice and Wistar rats: comparative study with nafadotride, U99194A and SB27701. Behav Pharmacol 15(4),253-262.
Kaiser R, et al. (2002). Relationship between adverse effects of antipsychotic treatment and dopamine D2 receptor polymorphisms in patients with schizophrenia. Molecular Psychiatry 7, 695-705.
Kling-Petersen T, et al. (1995). Effects on locomotor activity after local application of D3 preferring compounds in discrete areas of the rat brain. J Neural Transm Gen Sect 102(3), 209-20.
Lahiri & Nurnburger Jr (1991). A rapid non-enzymatic method for the preparation of HMV DNA from blood for RFLP analysis. Nucleic Acids Research 19, 5444.
Lerer B, et al. (2002). Pharmacogenetics of tardive dyskinesia: combined analysis of 780 patients supports association with dopamine D3 receptor gene Ser9Gly polymorphism. Neuropsychopharmacology 27(1), 105-119.
Lundstrom & Turpin (1996). Proposed schizophrenia-related gene polymorphism: expression of the Ser9Gly mutant human dopamine D3 receptor with the,Semliki Forest virus system. Biochem Biophys Res Commun 225(3), 1068-72.
Muller DJ, et al. (2001). Familial occurrence of tardive dyskinesia. Acta Psychiatr Scand 104(5), 375-9.
Muller DJ, et al. (2004). Clinical implications of pharmacogenomics for tardive dyskinesia. Pharmacogenomics Journal 4, 77-87.
Schooler& Kane (1982), Research diagnoses for tardive dyskinesia. Archives of General Psychiatry 39, 486-487.
Suzuki M, et al. (1998). D3 dopamine receptor mRNA is widely expressed in the human brain. Brain Res 779(1-2),58-74.
Tarsy & Baldessarini (2006). Epidemiology of tardive dyskinesia: is risk declining with modern antipsychotics? Movement Disorders. Published online: Mar. 10, 2006. DOI: 10.1002/mds.20823.
Uitenbroek DG (1997). "SISA-Binomial", available: http://home.clara.net/sisa/binomial.htm.

* cited by examiner

*Primary Examiner*—Sarae Bausch
*Assistant Examiner*—Katherine Salmon
(74) *Attorney, Agent, or Firm*—Suzannah K. Sundby, Esq.; Smith, Gambrell & Russell, LLP

(57) ABSTRACT

The present invention discloses markers for tardive dyskinesia. Also disclosed is a method of determining the risk of tardive dyskinesia from antipsychotic medication in a subject, the method comprising the step of genotyping a sample obtained from the subject for the rs905568 polymorphism, wherein a subject comprising a CC, CG or GC genotype is at increased risk for tardive dyskinesia as compared to a subject comprising the GG genotype. Kits for practicing the method are also disclosed.

11 Claims, No Drawings

```
                            SEQUENCE LISTING

<160> NUMBER OF SEQ ID NOS: 3

<210> SEQ ID NO 1
<211> LENGTH: 51
<212> TYPE: DNA
<213> ORGANISM: Homo Sapiens
<220> FEATURE:
<223> OTHER INFORMATION: RS9005568 polymorphism where s is c or g

<400> SEQUENCE: 1
ttgtgcaaaa ctgcaaatca gtgtcsagcg tgtgtagctg gcccagaggg c            51

<210> SEQ ID NO 2
<211> LENGTH: 51
<212> TYPE: DNA
<213> ORGANISM: Homo Sapiens
<220> FEATURE:
<223> OTHER INFORMATION: RS9005568 polymorphism with c at position 26

<400> SEQUENCE: 2
ttgtgcaaaa ctgcaaatca gtgtccagcg tgtgtagctg gcccagaggg c            51

<210> SEQ ID NO 3
<211> LENGTH: 51
<212> TYPE: DNA
<213> ORGANISM: Homo Sapiens
<220> FEATURE:
<223> OTHER INFORMATION: RS9005568 polymorphism with g at position 26

<400> SEQUENCE: 3
ttgtgcaaaa ctgcaaatca gtgtcgagcg tgtgtagctg gcccagaggg c            51
```

MARKER FOR TARDIVE DYSKINESIA

FIELD OF INVENTION

The present invention relates to polymorphisms in nucleotide sequences. More specifically, the present invention relates to polymorphisms in nucleotide sequences associated with tardive dyskinesia.

BACKGROUND OF THE INVENTION

Tardive dyskinesia (TD) is a side effect of chronic antipsychotic medication characterized by involuntary movements of the tongue, the orofacial region, trunk, and extremities. Its reported prevalence varies from 16% to 43%, with an annual incidence rate of around 5% (reviewed in Tarsy and Baldessarini, 2006). Patients with this condition often struggle with the immediate difficulties of motor function, but also with adhering to treatment, discrimination, and poorer quality of life, so predicting which patients are vulnerable to TD remains a high priority for psychiatrists in treatment selection. TD has a significant genetic component (Müller et al, 2001). Although such abnormal movements have been described before neuroleptics were given to patients, the etiology of TD remains unknown. A number of mechanisms have been hypothesized, including GABA insufficiency, free radical-mediated neuronal injury, and structural abnormalities in brain regions involved in motor function such as the caudate nucleus. A traditional hypothesis postulates TD as being caused by hypersensitivity of dopamine receptors induced by dopamine receptor antagonizing medications such as antipsychotics. In such a case, it is hypothesized that prolonged antagonism (or blocking) of dopamine receptors may induce a potentially irreversible increased affinity to dopamine. This results in an imbalance between inhibiting and activating mechanisms of the motor system a shift towards the activating mechanism and hence induce abnormal movements.

Molecular genetic studies investigating the role of the dopaminergic system in TD have been recently reviewed (Müller et al, 2004). Genes involved in the transportation (DAT1) or metabolism (MAOA, COMT, MAOB) of dopamine, have mainly produced negative findings in TD. D3 has received much attention in TD studies in light of several positive association results where the Ser9Gly polymorphism was found to be associated with TD (Lerer et al, 2002).

Anatomically, the dopamine receptor DRD3-coded D3 receptor is localized to the ventral striatum and putamen of the basal ganglia, an area of the brain that is involved in locomotor control (Suzuki et al, 1998). D3 receptor levels have been shown to increase in response to chronic haloperidol administration in rat brains (Buckland et al, 1992). The increase was also observed in human postmortem schizophrenia patient basal ganglia after neuroleptic treatment (D'Souza et al, 1997). R-(+)-7-OH-DPAT, a D3-selective agonist, inhibited locomotor activity when injected into the nucleus accumbens of rats (Kling-Petersen et al, 1995), while D3 antagonists increased motor activity (Gyertyan and Saghy, 2004). The findings were corroborated in mice lacking functional D3; they were hyperactive (Accili et al, 1996).

The Ser9Gly polymorphism was studied previously because of its role in D3 affinity for dopamine as revealed in CHO cells (Lundstrom and Turpin, 1996). Although these findings could not be replicated in other studies, the Gly allele (or Gly/Gly genotype) has been found associated with TD in a combined analysis involving 780 patients and in a subsequent meta-analysis including seven studies (Lerer et al, 2002) although the odds ratio for predicting risk is low at around 1.3. The mixed results among the different studies could be due to sample sizes, ethnic background differences or possibly by the lack of a comprehensive analysis of the DRD3 gene. Variations in the DRD3 gene, in addition to Ser9Gly, may contribute to TD risk or severity.

There is a need in the art for new genetic markers that are associated with tardive dyskinesia. Further, there is a need in the art for methods to determine if a subject is likely to develop tardive dyskinesia in response to antipsychotic drug therapy. Further, there is a need in the art for new screening methods to permit drugs or other pharmaceutical products to be tested on subjects susceptible to tardive dyskinesia from antipsychotic therapy.

SUMMARY OF THE INVENTION

The present invention relates to polymorphisms in nucleotide sequences. More specifically, the present invention relates to polymorphisms in nucleotide sequences associated with tardive dyskinesia.

According to the present invention there is provided a method of determining the risk of tardive dyskinesia from antipsychotic medication in a subject, the method comprising, genotyping a sample obtained from the subject for the rs905568 polymorphism, wherein a subject comprising a CC, CG or GC genotype is at increased risk for tardive dyskinesia as compared to a subject comprising the GG genotype.

Also provided by the present invention is a method as defined above, wherein the antipsychotic medication comprises a drug that affects dopamine signaling. In an embodiment, which is not meant to be limiting, the antipsychotic medication comprises clozapine, trifluoperazine, thioridazine, haloperidol, haloperidol decanoate, thiothixene, chlorpromazine, fluphenazine, loxapine, perphenazine, perphenazine decanoate, perphenazine-amitriptyline, acetophenazine, molindone, mesoridazine, fluphenazine decanoate, methotrimeprazine, risperidone, aripiprazole or a combination thereof. Further, but not wishing to be limiting in any manner, the present application is meant to encompass antipsychotic medication as defined by any subgroup of the compounds listed above.

Also provided by the present invention is a method as defined above, wherein the subject has or is suspected of having psychotic symptoms, disruptive behavior, disorganized thinking, symptoms of mania, or any combination thereof. Preferably, the subject is diagnosed by a trained medical professional.

Also provided by the present invention is a method as defined above, wherein the subject is a Caucasian subject.

The present invention also provides a method as defined above, wherein the sample is blood.

The present invention also provides a method of screening one or more drugs to prevent and/or treat tardive dyskinesia in a subject, the method comprising, a) genotyping the subject or group of subjects for the rs905568 polymorphism, the subject or subjects exhibiting at least one symptom of tardive dyskinesia;

b) administering the one or more drugs to the subject;

c) determining whether there is an improvement in tardive dyskinesia or one or more symptoms associated therewith, in the subject, and optionally;

determining whether the improvement is associated with a particular genotype of the rs905568 polymorphism.

The present invention also provides a kit comprising, a) one or more nucleic acid primers to amplify a nucleotide region, the nucleotide region comprising the putative rs905568 polymorphism;

b) one or more nucleic acid probes of between about 9 and 100 nucleotides that hybridize to the complement of the nucleotide sequence comprising the C variant or the G variant of the rs905568 polymorphism and including at least one nucleotide both upstream and downstream of the polymorphism, c) one or more reagents comprising buffer(s), dATP, dTTP, dCTP, dGTP, DNA polymerase(s), d) instructions for diagnosing or determining the risk of a subject to tardive dyskinesia from antipsychotic medication, e) one or more written documents and/or physical aids for assessing and/or quantifying abnormal involuntary movement, f) an abnormal involuntary movement scale or reference thereto, g) antipsychotic medication, h) instructions for using any component in the kit, or any combination thereof.

This summary of the invention does not necessarily describe all features of the invention.

DETAILED DESCRIPTION

The following description is of a preferred embodiment.

Tardive dyskinesia (TD) is a side effect of chronic antipsychotic medication. The etiology is unknown, but dopamine neurotransmission system changes have been suggested to be involved. Thus, a number of studies have focused on the association of TD and dopamine system gene polymorphisms, particularly the DRD3 gene. The role of DRD3 in TD is supported by gene expression and pharmacological studies. While there have been consistent positive finding between the Ser9Gly polymorphism of DRD3 and TD, there are also negative results. The present application provides results suggsting that a polymorphism in the region 5' of the DRD3 gene are associated with the development of tardive dyskinesia.

As described in greater detail in the Examples, the RS905568 polymorphism, thought to be present in region 5' of the DRD3 gene was tested for its association with TD in a subject sample population (N=93). The rs905568 polymorphism was significantly associated with TD (p=0.02) and quantitative AIMS scores (p=0.003). Thus, without wishing to be limiting or bound by theory in any manner, the present study suggests that DRD3 is involved in TD development.

The present invention provides a genetic marker that may be used to determine a subject's susceptibility to tardive dyskinesia. As described in more detail below, a specific polymorphism (RS905568) in the nucleotide sequence as shown in SEQ ID NO:1 may be used to determine if a subject is at risk of tardive dyskinesia from antipsychotic medication, for example, but not limited to, chronic antipsychotic medication. Specifically, subjects comprising the C nucleotide at position 26 in relation to the surrounding nucleotide sequence defined by SEQ ID NO: 1 are at increased risk for development of tardive dyskinesia from antipsychotic medication as compared to subjects that show only the G nucleotide at position 26. Further, the results provided herein suggest that in respect of the distribution of patients with the GG genotype versus C carriers, a trend for fewer tardive dyskinesia subjects was found with the GG genotype (p=0.082). Further, subjects with the GG genotype (AIMS score=3.00±2.63) were found to have significantly lower average AIMS scores compared to subjects who are C carriers (i.e having genotypes CC, CG or GC) (AIMS score=6.92±7.90).

By the term "RS905568 polymorphism" it is meant a nucleotide sequence comprising:

SEQ ID NO:1:

TTGTGCAAAACTGCAAATCAGTGTC(C/G)AGCGT-GTGTAGCTGGCCCAGAGGGC, a fragment thereof comprising the polymorphic site (C/G), or a nucleotide sequence that exhibits between 90% to 100% sequence identity thereto and comprises the polymorphic site (C/G), for example, but not limited to 90%, 91%, 92%, 93%, 94%, 95%, 96%, 97%, 98%, 99%, 100% or any value therein between. Further, the nucleotide sequences contemplated may comprise a range of sequence identities as provided by any two of the values listed, or any two values therein between. In respect of a fragment, it is preferred that the fragment comprises between about 9 and 51 consecutive nucleotides, for example 9, 11, 13, 15, 17, 19, 21, 23, 25, 30, 35, 40, 45, 50, 51 consecutive nucleotides or any value therein between, and further comprising the polymorphic site (C/G). Also contemplated are fragments that are defined by a range of nucleotide sizes as provided by any two of the values listed or any values therein between.

To determine whether a nucleic acid exhibits identity with the sequences presented herein, oligonucleotide alignment algorithms may be used, for example, but not limited to a BLAST, using default parameters: Program: blastn; Database: nr; Expect 10; filter: default; Alignment: pairwise; Query genetic Codes: Standard(1)), BLAST2 using default parameters: Matrix BLOSUM62; Filter: default, echofilter: on, Expect: 10, cutoff: default; Strand: both; Descriptions: 50, Alignments: 50), or FASTA, search, using default parameters.

The polymorphic site (C/G) is shown for SEQ ID NO:1 in bold parentheses. As will be evident to someone of skill in the art, the nucleotide sequence may be comprise either a C or a G at the position indicated by the parentheses, for example:

SEQ ID NO: 2:
TTGTGCAAAACTGCAAATCAGTGTC(C)AGCGTGTGTAGCTGGCCCAGAGG
GC or

SEQ ID NO: 3:
TTGTGCAAAACTGCAAATCAGTGTC(G)AGCGTGTGTAGCTGGCCCAGAGG
GC

It is known in the art that subjects may have one or more genotypes comprising a nucleotide sequence with a C or a G nucleotide at position 26, for example, but not limited to, as defined by SEQ ID NO:2 and SEQ ID NO:3, respectively. Without wishing to be considered limiting:

Subject 1 (exhibiting CC genotype):
                                                  (SEQ ID NO: 2)
TTGTGCAAAACTGCAAATCAGTGTC(C)AGCGTGTGTAGCTGGCCCAGAGG
GC (SEQ ID NO: 2)
TTGTGCAAAACTGCAAATCAGTGTC(C)AGCGTGTGTAGCTGGCCCAGAGG
GC Subject 2 (exhibiting a CG or GC genotype):
                                                  (SEQ ID NO: 2)
TTGTGCAAAACTGCAAATCAGTGTC(C)AGCGTGTGTAGCTGGCCCAGAGG
GC -continued

```
                                               (SEQ ID NO: 3)
TTGTGCAAAACTGCAAATCAGTGTC(G)AGCGTGTGTAGCTGGCCCAGAGG
GC

Subject 3 (exhibiting a GG genotype):
                                               (SEQ ID NO: 3)
TTGTGCAAAACTGCAAATCAGTGTC(G)AGCGTGTGTAGCTGGCCCAGAGG
GC (SEQ ID NO: 3)
TTGTGCAAAACTGCAAATCAGTGTC(G)AGCGTGTGTAGCTGGCCCAGAGG
GC
```

Other genotypes are also possible. Further, one or more additional polymorphisms may exist upstream or downstream of the polymorphic site that is in bold and in parentheses. Such nucleotide sequences are meant to be encompassed herein.

According to the present invention, there is provided a method of determining the risk of tardive dyskinesia from antipsychotic medication in a subject, the method comprising, genotyping a sample obtained from the subject for the rs905568 polymorphism, wherein a subject comprising a CC, CG or GC genotype is at increased risk for tardive dyskinesia as compared to a subject comprising the GG genotype.

The embodiment as provided above is meant to encompass a method of determining the risk of a subject developing tardive dyskinesia from antipsychotic medication, for example, but not limited to, meaning that the subject may have had few or no symptoms of tardive dyskinesia prior to or during therapy with antipsychotic medication. The embodiment is also meant to encompass a method of determining the risk of a subject to further worsening of tardive dyskinesia, for example, but not limited to one or more symptoms associated with tardive dyskinesia, from current or new antipsychotic medication.

By the term "antipsychotic medication", it is meant any drug, therapeutic, natural product, synthetic product, pharmaceutical product, composition or the like (collectively also referred herein to as drug or drugs) that may be employed to prevent and/or treat psychotic symptoms, disruptive behavior, disorganized thinking, symptoms of mania, or a combination thereof in a subject. Antipsychotic medication may comprise, but is not limited to, drugs that affect dopamine signaling, for example, drugs that may bind reversibly or irreversibly to one or more dopamine receptors, or that may act as competitive or non-competitive inhibitors to downregulate dopamine receptor signaling. In an embodiment, the antipsychotic medication comprises one or more of the following drugs: clozapine, trifluoperazine, thioridazine, haloperidol, haloperidol decanoate, thiothixene, chlorpromazine, fluphenazine, loxapine, perphenazine, perphenazine decanoate, perphenazine-amitriptyline, acetophenazine, molindone, mesoridazine, fluphenazine decanoate, methotrimeprazine, risperidone, aripiprazole, all of which are antipsychotics (modified from Casey and Gardos, 1986).

In an embodiment of the present invention, subjects from any ethnic race, age, gender or medical condition may be tested to determine if they are at risk for tardive dyskinesia from antipsychotic medication. In this regard, a healthy subject or a subject that does not have any symptoms of a disease or medical condition may be tested to determine if he or she is likely to develop tardive dyskinesia from antipsychotic medication. In this way, a proper course of treatment to minimize potential side effects to antipsychotic medication may be selected and/or administered to the subject in the event that such treatment is needed. Also, such a method may provide valuable information as to whether additional medication should be prescribed and/or administered to counteract tardive dyskinesia from antipsychotic medication. In a preferred embodiment, a subject diagnosed with a disease such as, but not limited to psychosis, schizophrenia, schizoaffective disorder or a combination thereof is tested to determine if antipsychotic medication is likely to promote or result in tardive dyskinesia.

As described above, but without wishing to be limiting in any manner the subject that is tested may comprise an individual with one or more psychotic symptoms, for example, but not limited to as described in DSM-IV which is hereby incorporated by reference. The psychotic symptoms may comprise positive symptoms such as, but not limited to distortions or exaggerations of inferential thinking (i.e. delusions), perception (i.e. hallucinations), language and communication (disorganised speech) and behavioral monitoring (grossly disorganized or catatonic behavior) or any combination thereof. Further, the positive symptoms may comprise distinct dimensions, for example, psychotic dimensions including, but not limited to delusions and hallucinations and disorganization dimensions including, but not limited to disorganized speech and behavior. It is also contemplated that the symptoms may comprise one or more negative symptoms, for example, but not limited to symptoms that reflect a diminution or loss of normal function. Further, the subject may exhibit a combination of both positive and negative symptoms. However, in a preferred embodiment, the subject that is tested has been diagnosed or suspected of having Schizophrenia or Schizoaffective Disorder. Any subject regardless of diagnosis who is treated, for example, but not limited to, with one or more of the following medications is at risk for Tardive Dyskinesia: clozapine, trifluoperazine, thioridazine, haloperidol, haloperidol decanoate, thiothixene, chlorpromazine, fluphenazine, loxapine, perphenazine, perphenazine decanoate, perphenazine-amitriptyline, acetophenazine, molindone, mesoridazine, fluphenazine decanoate, methotrimeprazine, risperidone, aripiprazole or a combination thereof.

Although the method of the present invention may be employed to determine whether any subject is susceptible to developing tardive dyskinesia in response to therapy with antipsychotic medication, in an embodiment of the present invention, which is not meant to be limiting in any manner, the method is practiced on a Caucasian or European Caucasian subject. However, the method of the present invention may be employed on subjects of other races or ethnicities as described previously.

The sample obtained from the subject may comprise any tissue or biological fluid sample from which genomic DNA may be obtained. For example, but not wishing to be limiting, DNA may be obtained from blood, hair follicle cells, skin cells, cheek cells, tissue biopsy, or the like. In a preferred embodiment, the sample is blood.

The DNA of the subject may be tested for the presence or absence of specific single nucleotide polymorphism (SNPs) in their DNA by any suitable technique known in the art. Representative techniques that may be employed include without limitation PCR analysis, sequencing, 5'exonuclease fluorescence assay, probe hybridization or a combination thereof.

Nucleotide sequences comprising polymorphisms may be genotyped using conventional techniques. For example, PCR using primers incorporating fluorescent probes is one suitable technique. For example, which is not to be considered limiting, primers having appropriate sequences upstream and downstream of the polymorphic site may be used to amplify the nucleotide regions comprising the polymorphisms.

The present invention also contemplates a method of screening one or more drugs to prevent and/or treat tardive dyskinesia in a subject, the method comprising,
 a) genotyping the subject or group of subjects exhibiting tardive dyskinesia for the rs905568 polymorphism,
 b) administering the one or more drugs to the subject;
 c) determining whether there is improvement in tardive dyskinesia or one or more symptoms associated therewith, in the subject, and optionally;
 determining whether the improvement in tardive dyskinesia is associated with a particular genotype of the rs905568 polymorphism.

It is to be understood that the method provided above may be practiced as indicated or in a different order. For example, step A) may be practiced after step B) or after step C but before determining whether the improvement in tardive dyskinesia is associated with a particular genotype of the rs905568 polymorphism. Other variations in the sequence of steps is also possible and meant to be encompassed by the present invention, as would be understood by a person of skill in the art.

The present invention also contemplates any drug identified by the method of screening as defined above. Further, the present invention contemplates the use of any drug identified by the method of screening as defined above that prevents or treats tardive dyskinesia or any symptom associated therewith.

Also provided by the present invention is a kit comprising one or more nucleic acid primers to amplify a nucleotide region, the nucleotide region comprising the putative rs905568 polymorphism; one or more nucleic acid probes of between about 9 and 100 nucleotides that hybridizes to the complement of the nucleotide sequence comprising the C variant or the G variant of the rs905568 polymorphism and preferably including at least one, more preferably three or more nucleotide both upstream and downstream of the polymorphism, one or more reagents including, but not limited to buffer(s), dATP, dTTP, dCTP, dGTP, DNA polymerase(s), instructions for diagnosing or determining the risk of a subject to tardive dyskinesia from antipsychotic medication, one or more written documents and/or physical aids for assessing and/or quantifying abnormal involuntary movement, an abnormal involuntary movement scale or reference thereto, antipsychotic medication, instructions for using any component in the kit, or any combination thereof.

The present invention will be further illustrated in the following examples.

EXAMPLES

Subjects and Methods

Informed consent was obtained before subjects' participation, and this study was approved by the Ethics Committee at the Centre for Addiction and Mental Health.

Subjects were recruited from the Center for Addiction and Mental Health in Toronto, Ontario (N=93). Subjects were selected based on their diagnoses for Schizophrenia or Schizoaffective Disorder according to DSM-III-R or IV (APA, 2000). All patients have undergone at least one year of treatment with typical antipsychotics. The presence of TD was assessed using the Abnormal Involuntary Movement Scale (AIMS) (Guy, 1976; Schooler and Kane, 1982). AIMS scores were available for all 93 patients for quantitative statistical analyses. All of them were European Caucasians, of which 38 were positive for the diagnosis of TD.

Gene Polymorphism Analysis

Genomic DNA was purified from whole blood samples using non-enzymatic method previously described (Lahiri and Numburger, 1991). 10 µL Polymerase Chain Reactions on 20 ng genomic DNA were performed using the rs905568 Assay-on-Demand (ABI) with the following conditions: 95° C. 10 min, followed by 60 cycles of 92° C. 15 sec, 60° C. 1 min. Genotyping was done after the subjects completed the follow-up. All laboratory staff were blind to the AIMS scores. Genotypes were determined using the ABI Prism® 7000 Sequence Detection System with the Allelic Discrimination program within the ABI software (Applied Biosystems, Foster City, Calif.). All ambiguous genotypes were retyped, and if they remained ambiguous, they were taken out of the analysis.

Statistics

Statistical analyses were conducted using the SPSS program Student version 10.0. Genotype frequency distribution was tested for fitness to Hardy-Weinberg equilibrium using Haploview. The association of genotype frequencies with age and AIMS was assessed using ANOVA and student t-test. Where the variances of AIMS scores among genotypes differed significantly using the Levene Test for Homogeneity of Variances, AIMS was tested with the Kruskal-Wallis test in place of ANOVA. Gender differences in genotype frequencies were assessed using the chi-square test. The differences in allele and genotype frequencies between patients with and without TD were analyzed by chi-square test. For contingency tables with at least one expected cell count of less than five, two-tailed Fisher's Exact Tests were performed (URL: World Wide Web at home.clara.net/sisa/fiveby2.htm; Uitenbroek, 1997).

Results

The genotype distribution of the rs905568 polymorphism did not differ significantly from the Hardy-Weinberg equilibrium ($p>0.05$). No significant association was found between genotype frequencies and gender ($p>0.05$). We also analyzed the correlation between AIMS scores and age, and found it to be positive ($r=0.262$) and significant ($p=0.01$).

We found the rs905568 allele frequencies to be significantly associated with TD diagnoses ($p=0.02$). The genotype frequencies of the same polymorphism were also associated with TD diagnoses ($p=0.05$). We further tested for an association between genotype frequencies and AIMS. Rs905568 showed a trend toward lower average AIMS scores in patients with the GG genotypes; however, the results from ANOVA did not reach statistical significance ($p=0.33$). When we compared the distribution of patients with the GG genotype versus C carriers, we found a trend for fewer tardive dyskinesia patients with the GG genotype ($p=0.082$). Further, we found the patients with the GG genotype ($3.00+/-2.63$) to have significantly lower average AIMS scores compared to patients who are C carriers ($6.92+/-7.90$) using the student t-test ($p=0.003$). The results are summarized in Table 1.

TABLE 1

Statistical analyses on demographics (sex, age) as well as total AIMS scores and TD diagnoses with genotypes and alleles of the RS905568 polymorphism in DRD3.

| DRD3 markers | | N (M/F) | Age (years) | Total AIMS score | TD (Yes/No) |
|---|---|---|---|---|---|
| RS905568 | 1/1 (C/C) | 31 (19/12) | 42.61 +/− 8.27 | 7.00 +/− 7.41 | 16/15 |
| | 1/2 (C/G) | 44 (25/19) | 42.77 +/− 9.86 | 6.86 +/− 8.32 | 15/29 |
| | 2/2 (G/G) | 10 (2/8) | 43.50 +/− 8.17 | 3.00 +/− 2.63 | 1/9 |
| | P-value | 0.076* | 0.965 | 0.331# | 0.052* |

| | | Allele 1 | Carrier of Allele 1 | |
|---|---|---|---|---|
| DRD3 markers | | TD (Yes/No) | TD (Yes/No) | AIMS |
| RS905568 | Yes | 47/59 | 31/44 | 6.92 +/− 7.90 |
| | No | 17/47 | 1/9 | 3.00 +/− 2.63 |
| | P-value | 0.0205 | 0.082 | 0.003 |

*Contingency table with at least one expected cell count of less than 5. Fisher's Exact Test was used.
Variances are significantly different among comparison groups by Levene's Test. Kruskel-Wallis Test was used.

Without wishing to be bound by theory or limiting in any manner, the results presented above showed that the region about 40 kb upstream of the DRD3 gene is associated with TD. Age, gender, and ethnicity have all been suggested to be risk factors for TD. TD occurrence and severity was found to increase with age, supporting previous studies from our laboratory and others (Basile et al, 1999; Kaiser et al, 2002). We have shown that age and gender were not likely responsible for the positive findings in this study, because mean age and gender proportions did not differ significantly among the genotypes of rs905568.

The DRD3 gene is unlikely the only genetically determined factor for TD. However, its function, which can be determined by variations in the promoter sequence, may play a significant role in determining TD risk and severity. In summary, we have found a genetic polymorphism in the upstream region of DRD3 to be associated with the serious and disfiguring side effect tardive dyskinesia.

REFERENCES

Accili D, Fishburn C S, Drago J, Steiner H, Lachowicz J E, Park B H, Gauda E B, Lee E J, Cool M H, Sibley D R, Gerfen C R, Westphal H, Fuchs S (1996). A targeted mutation of the D3 dopamine receptor gene is associated with hyperactivity in mice. Proc Natl Acad Sci USA 93(5), 1945-9.

APA (1994). Diagnostic and Statistical Manual of Mental Disorders (4th edn). Washington, D.C.: American Psychiatric Association.

Basile V S, Masellis M, Badri F, Paterson A D, Meltzer H Y, Lieberman J A, Potkin S G (1999). Association of the MscI polymorphism of the dopamine D3 receptor gene with tardive dyskinesia in schizophrenia. Neuropsychopharmacology 21, 17-27.

Buckland P R, O'Donovan M C, McGuffin P (1992). Changes in dopamine D1, D2 and D3 receptor mRNA levels in rat brain following antipsychotic treatment. Psychopharmacology (Berl) 106(4), 479-83.

Tardive dyskinesia and neuroleptics: from dogma to reason. Casey D E, Gardos G (ed). American Psychiatric Press, Inc., Washington D.C., USA, 1986. p 40.

D'Souza U, McGuffin P, Buckland P R (1997). Antipsychotic regulation of dopamine D1, D2 and D3 receptor mRNA. Neuropharmacology 36(11-12), 1689-96.

Guy W (1976). ECDEU Assessment Manual for Psychopharmacology (Revised edn). Washington, D.C.: Department of Health, Education and Welfare.

Gyertyan I, Saghy K (2004). Effects of dopamine D3 receptor antagonists on spontaneous and agonist-reduced motor activity in NMRI mice and Wistar rats: comparative study with nafadotride, U99194A and SB27701. Behav Pharmacol 15(4), 253-262.

Kaiser R, Tremblay P B, Klufmoller F, Roots I, Brockmoller J (2002). Relationship between adverse effects of antipsychotic treatment and dopamine D2 receptor polymorphisms in patients with schizophrenia. Molecular Psychiatry 7, 695-705.

Kling-Petersen T, Ljung E, Svensson K (1995). Effects on locomotor activity after local application of D3 preferring compounds in discrete areas of the rat brain. J Neural Transm Gen Sect 102(3), 209-20.

Lahiri D K, Nurnburger J I Jr (1991). A rapid non-enzymatic method for the preparation of HMV DNA from blood for RFLP analysis. Nucleic Acids Research 19, 5444.

Lerer B, Segman R H, Fangerau H, Daly A K, Basile V S, Cavallaro R, Aschauer H N, McCreadie R G, Ohlraun S, Ferrier N, Masellis M, Verga M, Scharfetter J, Rietschel M, Lovlie R, Levy U H, Meltzer H Y, Kennedy J L, Steen V M, Macciardi F (2002). Pharmacogenetics of tardive dyskinesia: combined analysis of 780 patients supports association with dopamine D3 receptor gene Ser9Gly polymorphism. Neuropsychopharmacology 27(1), 105-119.

Lundstrom K, Turpin M P (1996). Proposed schizophrenia-related gene polymorphism: expression of the Ser9Gly mutant human dopamine D3 receptor with the Semliki Forest virus system. Biochem Biophys Res Commun 225(3), 1068-72.

Müller D J, Schulze T G, Knapp M, Held T, Krauss H, Weber T, Ahle G, Maroldt A, Alfter D, Maier W, Nothen M M, Rietschel M (2001). Familial occurrence of tardive dyskinesia. Acta Psychiatr Scand 104(5), 375-9.

Müller D J, Shinkai T, De Luca V, Kennedy J L (2004). Clinical implications of pharmacogenomics for tardive dyskinesia. Pharmacogenomics Journal 4, 77-87.

Schooler N R, Kane J M (1982). Research diagnoses for tardive dyskinesia. Archives of General Psychiatry 39, 486-487.

Suzuki M, Hurd Y L, Sokoloff P, Schwartz J C, Sedvall G (1998). D3 dopamine receptor mRNA is widely expressed in the human brain. Brain Res 779(1-2), 58-74.

Tarsy D, Baldessarini R J (2006). Epidemiology of tardive dyskinesia: is risk declining with modern antipsychotics? Movement Disorders. Published online: 10 March, 2006. DOI: 10.1002/mds.20823.

Uitenbroek D G (1997). "SISA-Binomial", available: http://home.clara.net/sisa/binomial.htm.

All citations are hereby incorporated by reference.

The present invention has been described with regard to one or more embodiments. However, it will be apparent to persons skilled in the art that a number of variations and modifications can be made without departing from the scope of the invention as defined in the claims.

chlorpromazine, fluphenazine, loxapine, perphenazine, perphenazine decanoate, perphenazine-amitriptyline, acetophenazine, molindone, mesoridazine, fluphenazine decanoate, methotrimeprazine, risperidone, aripiprazole or a combination thereof.

4. The method of claim 1, wherein the subject has or is suspected of having psychosis, Schizophrenia, Schizoaffective disorder or any combination thereof.

5. The method of claim 1, wherein the sample is blood.

6. A method of screening for a drug which alleviates symptoms of tardive dyskinesia in a human subject which comprises, identifying a human subject as having an allele having a C corresponding to position 26 of SEQ ID No: 2 from a sample obtained from the subject who exhibits at least one

What is claimed is:

1. A method of identifying a human subject as having an increased risk of suffering from tardive dyskinesia which comprises,
    detecting the presence of an allele having a C corresponding to position 26 of SEQ ID NO:2 from a sample obtained from the subject, wherein the presence of the allele indicates the subject has an increased risk of suffering from tardive dyskinesia.

2. The method of claim 1, wherein the tardive dyskinesia is associated with the administration of a drug that affects dopamine signaling.

3. The method of claim 2, wherein the drug that affects dopamine signaling comprises clozapine, trifluoperazine, thioridazine, haloperidol, haloperidol decanoate, thiothixene, symptom of tardive dyskinesia, administering a drug to the subject, and determining whether the symptom is alleviated.

7. The method of claim 1, wherein the tardive dyskinesia is associated with the administration of a typical antipsychotic.

8. A method of identifying a human subject diagnosed with Schizophrenia or Schizoaffective disorder and treated with a typical antipsychotic as having an increased risk of suffering from tardive dyskinesia, which comprises,
    detecting the presence of an allele having a C corresponding to position 26 of SEQ ID NO:2 from a sample obtained from the subject, wherein the presence of the allele indicates the subject has an increased risk of suffering from tardive dyskinesia compared to a homozygous for the G allele corresponding to position 26 of SEQ ID NO:3.

9. The method of claim 1, wherein detecting the presence of the allele having a C corresponding to position 26 of SEQ ID NO:2 is conducted with a kit comprising a probe that hybridizes to the allele.

10. The method of claim 6, wherein detecting the presence of the allele having a C corresponding to position 26 of SEQ ID NO:2 is conducted with a kit comprising a probe that hybridizes to the allele.

11. The method of claim 8, wherein detecting the presence of the allele having a C corresponding to position 26 of SEQ ID NO:2 is conducted with a kit comprising a probe that hybridizes to the allele.

* * * * *